(12) United States Patent
Suddaby

(10) Patent No.: US 10,624,762 B2
(45) Date of Patent: Apr. 21, 2020

(54) BONE GRAFT DELIVERY DEVICE FOR MINIMALLY INVASIVE SURGERY

(71) Applicant: Loubert S. Suddaby, Orchard Park, NY (US)

(72) Inventor: Loubert S. Suddaby, Orchard Park, NY (US)

(73) Assignee: Orthorebirth USA, Georgetown, TX (US)

( * ) Notice: Subject to any disclaimer, the term of this patent is extended or adjusted under 35 U.S.C. 154(b) by 98 days.

(21) Appl. No.: 16/124,909

(22) Filed: Sep. 7, 2018

(65) Prior Publication Data

US 2020/0078065 A1  Mar. 12, 2020

(51) Int. Cl.
| | |
|---|---|
| *A61F 2/46* | (2006.01) |
| *A61B 17/88* | (2006.01) |
| *A61B 17/02* | (2006.01) |
| *A61B 17/34* | (2006.01) |
| *A61F 2/28* | (2006.01) |
| *A61B 17/00* | (2006.01) |

(52) U.S. Cl.
CPC ........ *A61F 2/4601* (2013.01); *A61B 17/0218* (2013.01); *A61B 17/3417* (2013.01); *A61B 17/3468* (2013.01); *A61B 17/8811* (2013.01); *A61F 2/2846* (2013.01); *A61B 2017/00314* (2013.01); *A61F 2002/2835* (2013.01); *A61F 2002/4635* (2013.01); *A61F 2002/4687* (2013.01)

(58) Field of Classification Search
CPC ........... A61B 2017/00292; A61B 2017/00314; A61B 17/02; A61B 17/0218; A61B 2017/0225; A61B 17/1631; A61B 17/1725; A61B 17/1796; A61B 2017/320032; A61B 17/3417; A61B 17/3431; A61B 17/3468; A61B 17/7019; A61B 17/7026; A61B 17/7028; A61B 17/7029; A61B 17/7031; A61B 17/8811; A61B 17/8861; A61F 2002/2835; A61F 2/2846; A61F 2/46; A61F 2/4601; A61F 2002/4635; A61F 2002/4687
See application file for complete search history.

(56) References Cited

U.S. PATENT DOCUMENTS

| | | |
|---|---|---|
| 5,295,980 A | 3/1994 | Ersek |
| 5,360,416 A | 11/1994 | Ausherman et al. |

(Continued)

FOREIGN PATENT DOCUMENTS

| | | | | |
|---|---|---|---|---|
| FR | 2606267 | * | 5/1988 | |
| FR | 2606267 A1 | * | 5/1988 | ........... A61B 17/164 |

*Primary Examiner* — Larry E Waggle, Jr.
(74) *Attorney, Agent, or Firm* — Simpson & Simpson, PLLC

(57) ABSTRACT

A bone graft delivery device, including a dilator sheath arranged to be connected to a first transverse process, the dilator sheath having a first window, a ramp guide removably engageable with the dilator sheath and arranged to be connected to the first transverse process, the ramp guide including a second window and a ramp at least partially connected to the second window, a snake sheath, and a snake arranged to feed the snake sheath through the ramp guide and out of the first and second windows toward a second transverse process, the second transverse process being adjacent to the first transverse process.

20 Claims, 14 Drawing Sheets

(56) References Cited

U.S. PATENT DOCUMENTS

| | | | |
|---|---|---|---|
| 5,972,013 | A | 10/1999 | Schmidt |
| 6,746,451 | B2 | 6/2004 | Middleton et al. |
| 6,923,813 | B2 | 8/2005 | Phillips et al. |
| 7,241,297 | B2 | 7/2007 | Shaolian et al. |
| 7,503,920 | B2 | 3/2009 | Siegal |
| 7,901,407 | B2 | 3/2011 | Olson, Jr. et al. |
| 8,827,981 | B2 * | 9/2014 | Liu .................... A61B 17/8811 604/506 |
| 8,974,506 | B2 * | 3/2015 | Wenger ................ A61C 8/0012 606/304 |
| 9,232,937 | B2 | 1/2016 | Alleyne |
| 9,247,952 | B2 | 2/2016 | Bleich et al. |
| 9,295,479 | B2 | 3/2016 | Hibri et al. |
| 9,717,507 | B2 | 8/2017 | Patel et al. |
| 2003/0158566 | A1 | 8/2003 | Brett |
| 2004/0044350 | A1 | 3/2004 | Martin et al. |
| 2004/0044412 | A1 * | 3/2004 | Lambrecht ........... A61B 5/1076 623/17.16 |
| 2005/0124999 | A1 | 6/2005 | Teitelbaum et al. |
| 2005/0197661 | A1 | 9/2005 | Carrison et al. |
| 2005/0209557 | A1 | 9/2005 | Carroll et al. |
| 2005/0216018 | A1 | 9/2005 | Sennett |
| 2006/0004369 | A1 | 1/2006 | Patel et al. |
| 2006/0142732 | A1 | 6/2006 | Karmarkar et al. |
| 2013/0345709 | A1 | 12/2013 | Burger et al. |
| 2016/0106551 | A1 | 4/2016 | Grimberg, Jr. et al. |
| 2017/0238984 | A1 | 8/2017 | Kleiner |

* cited by examiner

BONE GRAFT DELIVERY DEVICE FOR MINIMALLY INVASIVE SURGERY

FIELD

The present disclosure relates to surgical fusion of the spine typically employed in orthopedic or neurosurgical procedures to establish long term spinal stability, and more particularly, a bone graft delivery system, and even more particularly, a bone graft delivery device for interbody or paraspinal placement of bone graft materials to facilitate spinal fusion via a minimally invasive approach.

BACKGROUND

Of all animals possessing a backbone, human beings are the only creatures who remain upright for significant periods of time. From an evolutionary standpoint, this erect posture has conferred a number of strategic benefits, not at least of which is freeing the upper limbs for purposes other than locomotion. From an anthropologic standpoint, it is also evident that this unique evolutionary adaption is a relatively recent change, and as such has not benefited from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvis or sacral region which are normally fused together and form the back part of the pelvis. This column of bones is critical for protecting the delicate spinal cord and nerves and for providing structural support for the entire body.

Between the vertebral bones themselves exist soft tissue structures, or discs, composed of fibrous tissue and cartilage which are compressible and act as shock absorbers for sudden downward forces on the upright column. The discs allow the bones to move independently of each other, as well. The repetitive forces which act on these intervertebral discs during repetitive day-to-day activities of bending, lifting, and twisting cause them to break down or degenerate over time.

Presumably because of humans' upright posture, their intervertebral discs have a high propensity to degenerate. Overt trauma, or covert trauma occurring in the course of repetitive activities disproportionately affect the more highly mobile areas of the spine. Disruption of a disc's internal architecture leads to bulging, herniation, or protrusion of pieces of disc and eventual disc space collapse. Resulting mechanical and even chemical irritation of surrounding neural elements (spinal cord and nerves) cause pain, attended by varying degrees of disability. In addition, loss of disc height relaxes tension on the longitudinal spinal ligaments thereby contributing to varying degrees of spinal degenerative instability such as spinal curvature.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While interbody and instrumented posterolateral fusions are well known in the art, and frequently performed, one recurring problem accompanying these procedures is the accurate placement of the bone graft to ensure a long term stable arthrodesis. Hardware placement alone will not suffice as metal fatigue will eventually result in the breakage, loosening, or subsidence of virtually any spinal hardware not supported by a bone fusion mass.

While it is relatively easy to place bone graft material in open spinal fusion procedures, it is much more difficult to place adequate bone graft in situations where minimally invasive techniques are employed as the access channel to the spine is generally not much larger than that required to place the hardware percutaneously.

Percutaneous placement of pedicle screws is frequently employed either as a primary method of utilizing stabilizing hardware or as a back up to an interbody fusion. While it is relatively easy to place pedicle screws percutaneously under fluoroscopic guidance, and pass a connecting rod between pedicle screws, it is much more difficult to decorticate the laterally placed transverse processes and place bridging bone graft along them without enlarging the percutaneous incisions substantially or essentially converting the operation to a de facto open Wiltse approach, which requires a sizable incision and defeats the purpose of percutaneously placed minimally invasive pedicle screws.

Thus, there is a long felt need for a device that allows placement of adequate bone graft prior to or after a minimally invasive instrumented spinal fusion such that a stable long term arthrodesis can occur, wherein conversion to an open approach is not necessary simply to place adequate bone graft material.

SUMMARY

According to aspects illustrated herein, there is provided a bone graft delivery device, comprising a dilator sheath arranged to be connected to a first transverse process, the dilator sheath having a first window, a ramp guide removably engageable with the dilator sheath and arranged to be connected to the first transverse process, the ramp guide comprising a second window and a ramp at least partially connected to the second window, a snake sheath, and a snake arranged to feed the snake sheath through the ramp guide and out of the first and second windows toward a second transverse process, the second transverse process being adjacent to the first transverse process.

According to aspects illustrated herein, there is provided a bone graft delivery device, comprising a dilator sheath arranged to be connected to a first transverse process, the dilator sheath having a first window arranged to be directed to a second transverse process, the second transverse process being adjacent to the first transverse process, a ramp guide removably engageable with the dilator sheath and arranged to be connected to the first transverse process, the ramp guide comprising, a lateral wall, a first end, a second end, a second window arranged between the first and second ends, and a ramp at least partially connected to the second window and arranged within the lateral wall, a snake sheath, and a snake arranged to feed the snake sheath through the ramp guide and out of the first and second windows to the second transverse process.

It is an object of the present disclosure to either fill an implanted interbody device with bone graft, or more particularly, to place bone graft in a paraspinal position, either lamina to lamina or transverse process to transverse process such that long term spinal arthrodesis can occur consequential to the performance of a minimally invasive instrumented spinal fusion.

It is also an object of the present disclosure to have a device that is easy to use, capable of placing a variety of different graft material, and compatible with present minimally invasive techniques known in the art.

To achieve these objects, a Kirschner wire (K-wire) is placed through the incision made to insert a percutaneous cannulated pedicle screw. It should be noted that the bone graft insertion device of the present disclosure can be employed and graft material inserted either prior to or after placement of spinal hardware.

The K-wire is placed under fluoroscopic control onto the body of a transverse process designated for fusion. Sequential tubular tissue dilators are placed over the K-wire, with the final dilator having, for example, an internal diameter of 8-10 mm.

The final dilator is held in apposition onto the surface of the transverse process and the K-wire and other dilators are removed. A tubular rasp is inserted and twisted clockwise and counter clockwise to decorticate the transverse process. This process is repeated at the adjacent transverse process to be fused.

The rasp is removed from the final dilator and a ramp guide is placed into the dilator sheath. The dilator sheath has a lateral window at its distal end and the window is directed toward the adjacent transverse process. The ramp guide ensures that any object placed down the dilator sheath will be directed to exit the lateral window at an angle of, for example, approximately 90°.

A unidirectional snake contained in a flexible clear plastic sheath is inserted into the ramp guide. By unidirectional it is meant that the snake flexes in a single preferred direction but not in any other direction similar to the distal phalangeal joints in the finger digit. The snake mobility is further restricted such that it cannot flex more than 90° from its insertion axis.

The snake and sheath are inserted down the ramp guide tube and advanced toward the transverse process. Once the snake and its sheath engage the ramp, the snake and sheath are biased to exit the window in the side wall of the dilator sheath at approximately a 90° angle.

Further advancement of the snake sheath complex advances it toward the adjacent transverse processes. Radiographic markers in the sheath allow this process to be followed under fluoroscopic control.

Once the snake sheath complex is advanced to the level of the adjacent transverse process, it abuts the dilator sheath at that level which can be recognized both through tactile feedback and fluoroscopic visualization. The adjacent dilator sheath is then withdrawn a sufficient distance to allow the snake sheath complex to slide between it and the decorticated transverse process. The snake sheath is now visible through the second dilator sheath tube.

Once positioned from transverse process to transverse process, the snake is removed, leaving the snake sheath in position from one transverse process to the other. Bone graft is introduced into the snake sheath sufficient to bridge the distance between the transverse processes. The snake is then introduced into the snake sheath and the bone graft material is pushed along and through the snake sheath.

Once the bone graft is visualized in the sheath overlying the adjacent transverse process, the snake is held in position and the sheath is gradually withdrawn, leaving the bone graft material in situ.

The snake, snake sheath, and ramp guide are then fully withdrawn, leaving the two dilator sheaths in position so that additional bone graft can be applied if desired.

The dilator sheaths are then removed leaving the bone graft in ideal position extending from one transverse process to the other.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be appreciated that facet joints are a set of synovial, plane joints between the articular processes of two adjacent vertebrae. There are two facet joints in each spinal motion segment and each facet joint is innervated by the recurrent meningeal nerves.

By "non-rotatably connected" elements, we mean that: the elements are connected so that whenever one of the elements rotate, all the elements rotate; and relative rotation between the elements is not possible. Radial and/or axial movement of non-rotatably connected elements with respect to each other is possible, but not required. By "rotatably connected" elements, we mean that the elements are rotatable with respect to each other.

Figure 1:
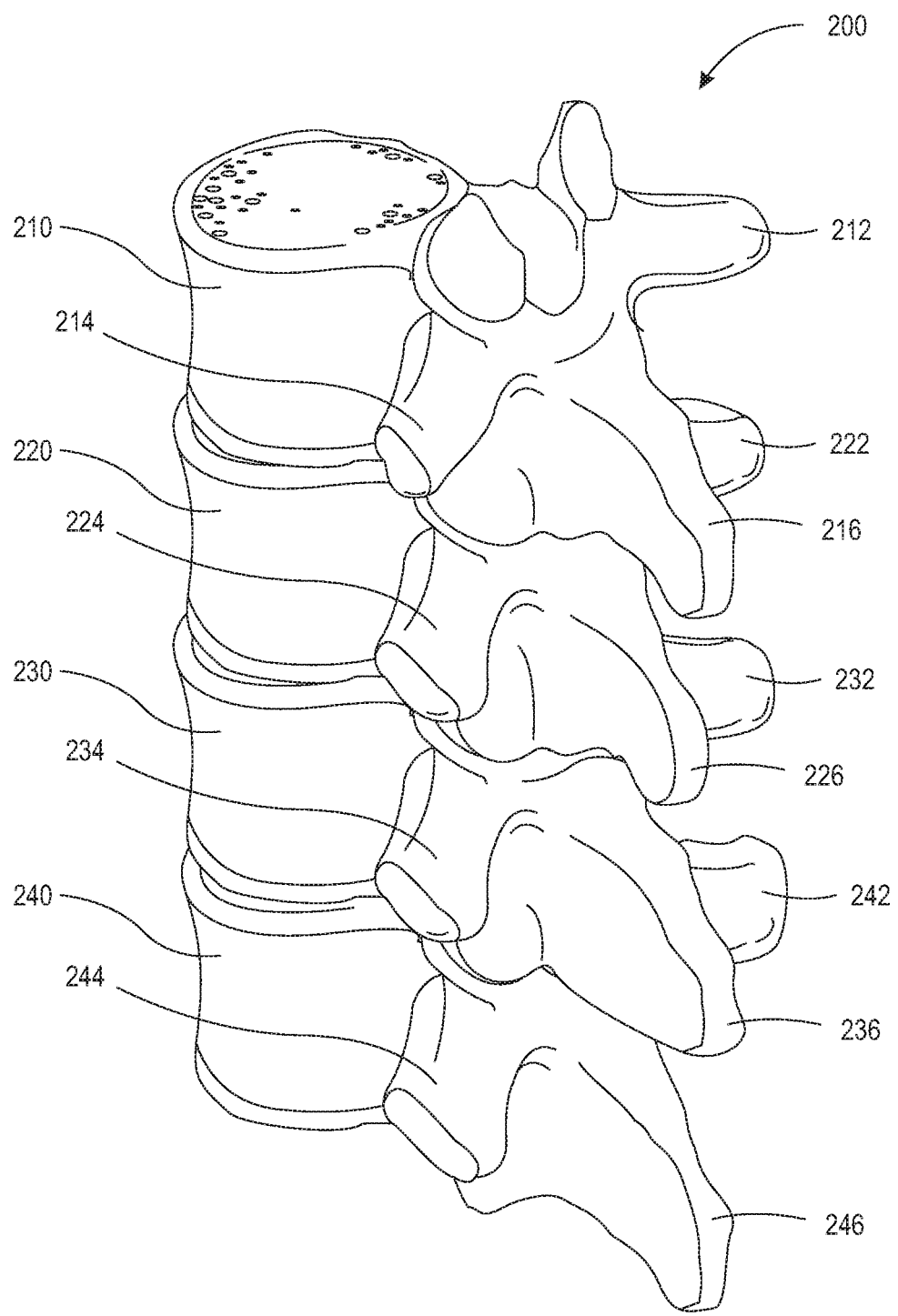
FIG. 1 is a perspective view of a spinal column.

Referring now to the figures, FIG. 1 is a perspective view of spinal column 200. Spinal column 200 generally comprises vertebra 210, 220, 230, and 240. It should be appreciated that spinal column 200 is the spinal column of a human or other animal having a spinal column. The typical human comprises thirty-three vertebrae interlocked with each other to form the spinal column. For the purposes of this description, spinal column 200 is only depicted as having four vertebrae. Vertebra 210 comprises transverse process 212, transverse process 214, and spinous process 216. Vertebra 220 is arranged adjacent to vertebra 210 and comprises transverse process 222, transverse process 224, and spinous process 226. Vertebra 230 is arranged adjacent to vertebra 220 and comprises transverse process 232, transverse process 234, and spinous process 236. Vertebra 240 is arranged adjacent to vertebra 230 and comprises transverse process 242, transverse process 244, and spinous process 246.

Figure 2A:
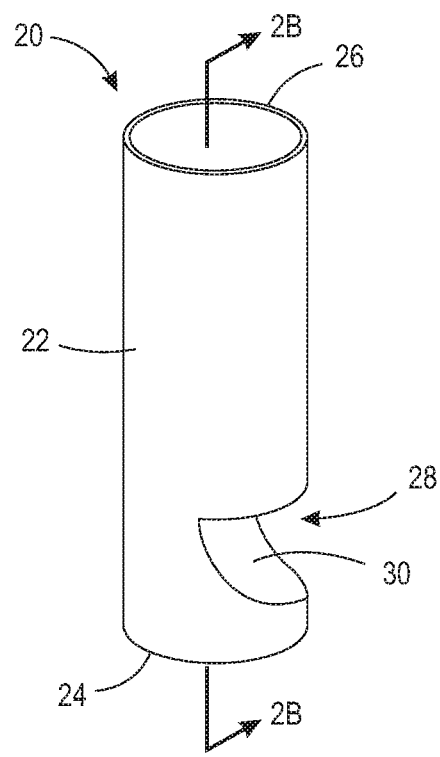
FIG. 2A is a perspective view of a ramp guide.
Figure 2B:
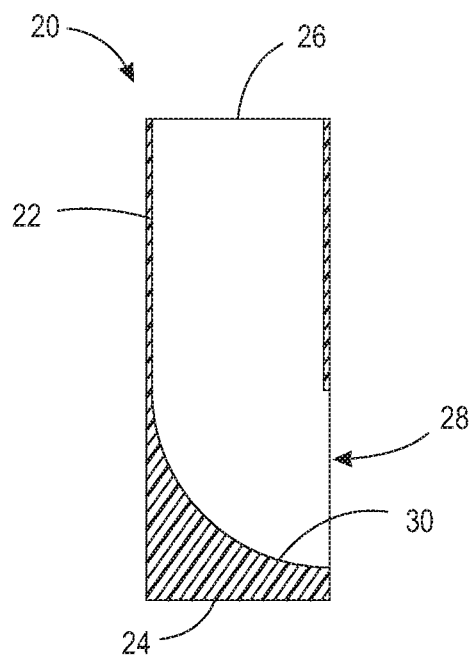
FIG. 2B is a cross-sectional view of the ramp guide taken generally along line 2B-2B in FIG. 2A.

FIG. 2A is a perspective view of ramp guide 20. FIG. 2B is a cross-sectional view of ramp guide 20 taken generally along line 2B-2B in FIG. 2A. Ramp guide 20 comprises lateral wall 22, end 24, and end 26. Ramp guide 20 is shown being generally cylindrical having a circular cross-section. It should be appreciated, however, that ramp guide 20 may comprise any suitable geometric cross-section, for example, square, rectangular, ovular, ellipsoidal, trapezoidal, etc., and that this disclosure should not be limited to the embodiment shown. Lateral wall 22 further comprises window 28 arranged between end 24 and end 26. Ramp guide 20 further comprises ramp 30 arranged within lateral wall 22. Ramp 30 extends from window 28 proximate end 24 in a direction toward end 26 to lateral wall 22, as shown in FIG. 2B. Ramp guide 20 is arranged to be inserted into dilator sheath 10, as will be discussed in greater detail below. End 26 is open such that snake 40 and snake sheath 60 may be inserted therein, as will be discussed in greater detail below. End 24 may be open or closed. In some embodiments, the area between 24 and ramp 30 is filled with material and is a solid. In some embodiments, the area between 24 and 30 is not filled with material and forms a hollow shell.

Figure 3A:
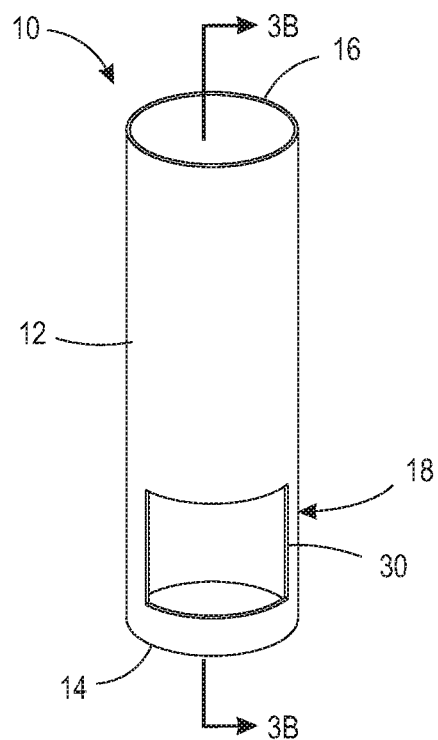
FIG. 3A is a perspective view of a dilator sheath.
Figure 3B:
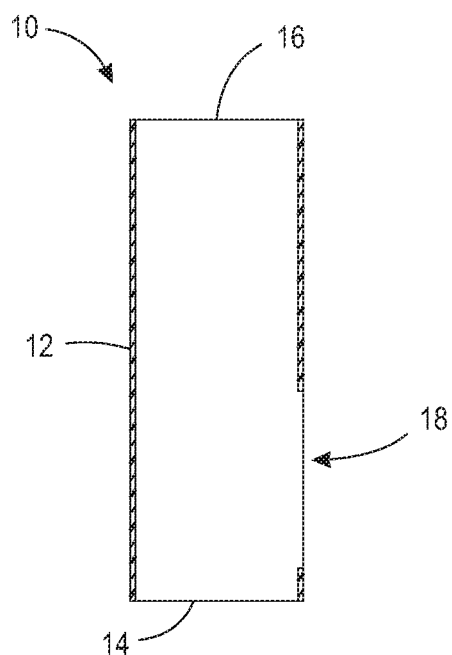
FIG. 3B is a cross-sectional view of the dilator sheath taken generally along line 3B-3B in FIG. 3A.

FIG. 3A is a perspective view of dilator sheath 10. FIG. 3B is a cross-sectional view of dilator sheath 10 taken generally along line 3B-3B in FIG. 3A. Dilator sheath 10 comprises lateral wall 12, end 14, and end 16. Dilator sheath 10 is shown being generally cylindrical having a circular cross-section. It should be appreciated, however, that dilator sheath 10 may comprise any suitable geometric cross-section, for example, square, rectangular, ovular, ellipsoidal, trapezoidal, etc., and that this disclosure should not be limited to the embodiment shown. Dilator sheath 10 and ramp guide 20 should comprise substantially the same geometric cross-section, with ramp guide 20 be suitable to be arranged within lateral wall 12 of dilator sheath 10. Lateral wall 12 further comprises window 18 arranged between end 14 and end 16. Window 18 is arranged to align with window 28 of ramp guide 20 when engaged therewith. End 16 is an open top such that ramp guide 20 may be inserted therein, as will be discussed in greater detail below. End 24 is an open bottom such that additional bone graft material can be positioned on the primary transverse process, as will be discussed in greater detail below.

Figure 4A:
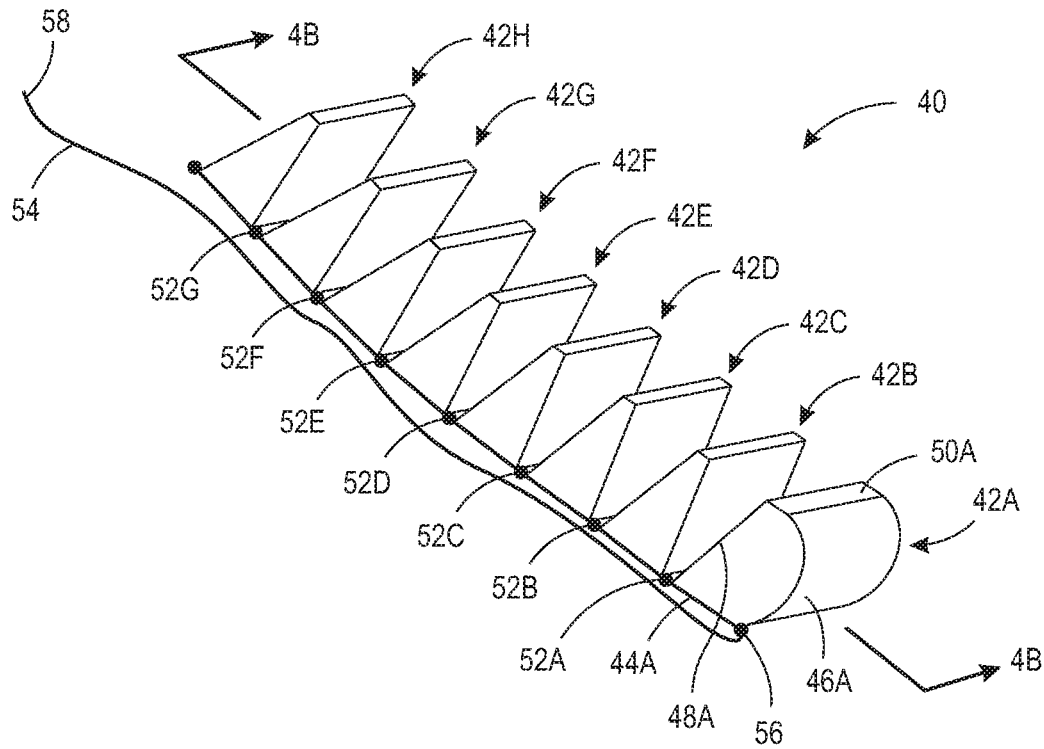
FIG. 4A is a perspective view of a snake.
Figure 4B:
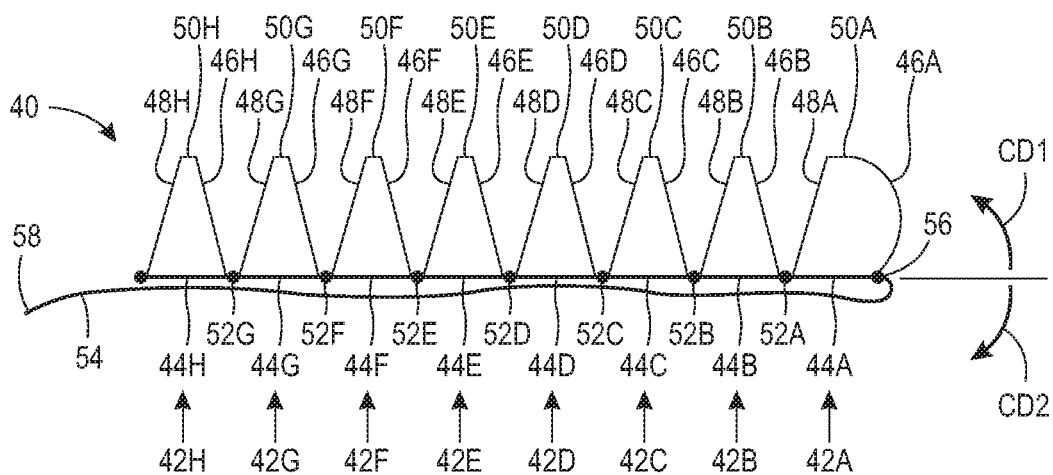
FIG. 4B is a cross-sectional view of the snake taken generally along line 4B-4B in FIG. 4A.

FIG. 4A is a perspective view of snake 40. FIG. 4B is a cross-sectional view of snake 40 taken generally along line 4B-4B in FIG. 4A. Snake 40 is an articulated flexible tool that is fed through ramp guide 20, out windows 18 and 28 such that it extends from the primary transverse process to the adjacent transverse process. Snake 40 generally comprises sections 42A-H interconnected by respective hinges 52A-G. The shape of sections 42A-H (e.g., trapezoidal or triangular) along with arrangement of hinges 52A-G allow snake 40 to flex only in one direction, i.e., unidirectional. By unidirectional, it is meant that snake 40 flexes in a single preferred direction but not in any other direction similar to the distal phalangeal joints in the finger digit. Snake 40 may be further restricted such that it cannot flex more than 90° from its insertion axis. It should be appreciated that snake 40 may have any number of sections (e.g., one or more sections) suitable to drive and/or feed snake sheath 60 and bone graft material from the primary transverse process to the adjacent transverse process. Snake 40 is illustrated comprising eight sections; however this disclosure should not be limited to the embodiment shown.

Section 42A comprises bottom side 44A, front side 46A, rear side 48A, and top side 50A. Sides 44A, 46A, 48A, 50A may be planar or curvilinear. In the embodiment shown, sides 44A, 48A, and 50A are planar and side 46A is curvilinear. Front side 46A is a solid wall arranged to be inserted into end 26 of ramp guide 20. In some embodiments, sides 44A, 46A, 48A, and 50A are solid walls that enclose section 42A. In some embodiments, sides 44A, 48A, and 50A may not be solid walls, but rather section 42A may form a cage, or a structure of bars or wires. Front side 46A is arranged to drive or feed snake sheath 60 through ramp guide 20 from the primary transverse process to the adjacent transverse process, as will be discussed in greater detail below.

Section 42B is connected to section 42A and comprises bottom side 44B, front side 46B, rear side 48B, and top side 50B. Sides 44B, 46B, 48B, and 50B may be planar or curvilinear. In the embodiment shown, sides 44B, 46B, 48B, and 50B are planar. In some embodiments, sides 44B, 46B, 48B, and 50B are solid walls that enclose section 42B. In some embodiments, sides 44B, 46B, 48B, and 50B may not be solid walls, but rather section 42B may form a cage, or a structure of bars or wires. In the embodiment shown, section 42B is hingedly connected to section 42A via hinge 52A. Hinge 52A allows, from the position shown in FIG. 4B, angular movement of section 42A relative to section 44B in circumferential direction CD1, but prevents movement of section 42A relative to section 44B in circumferential direction CD2. Thus, as shown in FIG. 4A, hinge 52A is in a fully opened state and closes as bottom side 44A is displaced in circumferential direction CD1 relative to bottom side 44B. For example, bottom side 44A may be angled from zero to ninety degrees relative to bottom side 44B.

Section 42C is connected to section 42B and comprises bottom side 44C, front side 46C, rear side 48C, and top side 50C. Sides 44C, 46C, 48C, and 50C may be planar or curvilinear. In the embodiment shown, sides 44C, 46C, 48C, and 50C are planar. In some embodiments, sides 44C, 46C, 48C, and 50C are solid walls that enclose section 42C. In some embodiments, sides 44C, 46C, 48C, and 50C may not be solid walls, but rather section 42C may form a cage, or a structure of bars or wires. In the embodiment shown, section 42C is hingedly connected to section 42B via hinge 52B. Hinge 52B allows, from the position shown in FIG. 4B, angular movement of section 42B relative to section 44C in circumferential direction CD1, but prevents movement of section 42B relative to section 44C in circumferential direction CD2. Thus, as shown in FIG. 4A, hinge 52B is in a fully opened state and closes as bottom side 44B is displaced in circumferential direction CD1 relative to bottom side 44C. For example, bottom side 44B may be angled from zero to ninety degrees relative to bottom side 44C.

Section 42D is connected to section 42C and comprises bottom side 44D, front side 46D, rear side 48D, and top side 50D. Sides 44D, 46D, 48D, and 50D may be planar or curvilinear. In the embodiment shown, sides 44D, 46D, 48D, and 50D are planar. In some embodiments, sides 44D, 46D, 48D, and 50D are solid walls that enclose section 42D. In some embodiments, sides 44D, 46D, 48D, and 50D may not be solid walls, but rather section 42D may form a cage, or a structure of bars or wires. In the embodiment shown, section 42D is hingedly connected to section 42C via hinge 52C. Hinge 52C allows, from the position shown in FIG. 4B, angular movement of section 42C relative to section 44D in circumferential direction CD1, but prevents movement of section 42C relative to section 44D in circumferential direction CD2. Thus, as shown in FIG. 4A, hinge 52C is in a fully opened state and closes as bottom side 44C is displaced in circumferential direction CD1 relative to bottom side 44D. For example, bottom side 44C may be angled from zero to ninety degrees relative to bottom side 44D.

Section 42E is connected to section 42D and comprises bottom side 44E, front side 46E, rear side 48E, and top side 50E. Sides 44E, 46E, 48E, and 50E may be planar or curvilinear. In the embodiment shown, sides 44E, 46E, 48E, and 50E are planar. In some embodiments, sides 44E, 46E, 48E, and 50E are solid walls that enclose section 42E. In some embodiments, sides 44E, 46E, 48E, and 50E may not be solid walls, but rather section 42E may form a cage, or a structure of bars or wires. In the embodiment shown, section 42E is hingedly connected to section 42D via hinge 52D. Hinge 52D allows, from the position shown in FIG. 4B, angular movement of section 42D relative to section 44E in circumferential direction CD1, but prevents movement of section 42D relative to section 44E in circumferential direction CD2. Thus, as shown in FIG. 4A, hinge 52D is in a fully opened state and closes as bottom side 44D is displaced in circumferential direction CD1 relative to bottom side 44E. For example, bottom side 44D may be angled from zero to ninety degrees relative to bottom side 44E.

Section 42F is connected to section 42E and comprises bottom side 44F, front side 46F, rear side 48F, and top side 50F. Sides 44F, 46F, 48F, and 50F may be planar or curvilinear. In the embodiment shown, sides 44F, 46F, 48F, and 50F are planar. In some embodiments, sides 44F, 46F, 48F, and 50F are solid walls that enclose section 42F. In some embodiments, sides 44F, 46F, 48F, and 50F may not be solid walls, but rather section 42F may form a cage, or a structure of bars or wires. In the embodiment shown, section 42F is hingedly connected to section 42E via hinge 52E. Hinge 52E allows, from the position shown in FIG. 4B, angular movement of section 42E relative to section 44F in circumferential direction CD1, but prevents movement of section 42E relative to section 44F in circumferential direction CD2. Thus, as shown in FIG. 4A, hinge 52E is in a fully opened state and closes as bottom side 44E is displaced in circumferential direction CD1 relative to bottom side 44F. For example, bottom side 44E may be angled from zero to ninety degrees relative to bottom side 44F.

Section 42G is connected to section 42F and comprises bottom side 44G, front side 46G, rear side 48G, and top side 50G. Sides 44G, 46G, 48G, and 50G may be planar or curvilinear. In the embodiment shown, sides 44G, 46G, 48G, and 50G are planar. In some embodiments, sides 44G, 46G, 48G, and 50G are solid walls that enclose section 42G. In some embodiments, sides 44G, 46G, 48G, and 50G may not be solid walls, but rather section 42G may form a cage, or a structure of bars or wires. In the embodiment shown, section 42G is hingedly connected to section 42F via hinge 52F. Hinge 52F allows, from the position shown in FIG. 4B, angular movement of section 42F relative to section 44G in circumferential direction CD1, but prevents movement of section 42F relative to section 44G in circumferential direction CD2. Thus, as shown in FIG. 4A, hinge 52F is in a fully opened state and closes as bottom side 44F is displaced in circumferential direction CD1 relative to bottom side 44G. For example, bottom side 44F may be angled from zero to ninety degrees relative to bottom side 44G.

Section 42H is connected to section 42G and comprises bottom side 44H, front side 46H, rear side 48H, and top side 50H. Sides 44H, 46H, 48H, and 50H may be planar or curvilinear. In the embodiment shown, sides 44H, 46H, 4811, and 5011 are planar. In some embodiments, sides 4411, 4611, 4811, and 5011 are solid walls that enclose section 4211. In some embodiments, sides 4411, 4611, 4811, and 5011 may not be solid walls, but rather section 4211 may form a cage, or a structure of bars or wires. In the embodiment shown, section 4211 is hingedly connected to section 42G via hinge 52G. Hinge 52G allows, from the position shown in FIG. 4B, angular movement of section 42G relative to section 4411 in circumferential direction CD1, but prevents movement of section 42G relative to section 4411 in circumferential direction CD2. Thus, as shown in FIG. 4A, hinge 52G is in a fully opened state and closes as bottom side 44G is displaced in circumferential direction CD1 relative to bottom side 4411. For example, bottom side 44G may be angled from zero to ninety degrees relative to bottom side 4411.

Snake 40 may further comprise cord 54. Cord 54 comprises end 56 and end 58. End 56 is connected to, for example, section 42A. The user (e.g., surgeon) may utilize cord 54 in order to prevent snake 40 from over flexing in circumferential direction CD1 as snake 40 travels from the primary transverse process to the adjacent transverse process. For example, if tissue causes the sections of snake 40 to displace excessively in circumferential direction CD1, the user pulls on end 58 to pull the sections back in circumferential direction CD2. Cord 54 may be a wire, string, rope, cable, or any other suitable tensioning means. It should be appreciated that cord 54 may be connected to a section of snake 40 other than section 42A, for example, section 42B. Additionally, it should be appreciated that snake 40 may have one or more cords connected to the same section or various sections of snake 40.

Figure 5:
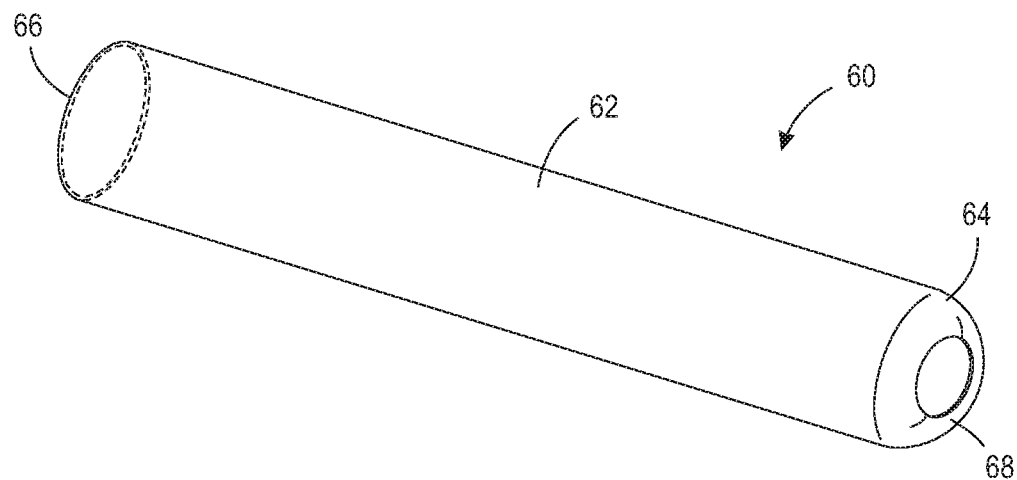
FIG. 5 is a perspective view of a snake sheath.

FIG. 5 is a perspective view of snake sheath 60. Snake sheath 60 is generally cylindrical and comprises lateral wall 62, end 64, end 66, and flange 68. It should be appreciated that snake sheath 60 may comprise any suitable geometric shape (e.g., snake 60 may comprise an ovular, an ellipsoidal, a rectangular, or a square cross-section). Snake sheath 60 is a clear or transparent plastic sheath. In some embodiments, snake sheath 60 is translucent or opaque. In some embodiments, snake sheath 60 comprises another suitable material, for example, malleable metal. Flange 68 is connected to and extends radially inward from end 64. Snake sheath 60 is arranged to be fed, using snake 40, down through ramp guide 20, with end 64 inserted first, and from the primary transverse process to the adjacent transverse process, as will be discussed in greater detail below. Specifically, flange 68 is arranged to abut against or catch on front surface 46A of snake 40. Once snake sheath 60 is fully inserted (i.e., from end 26 of ramp guide 20 to the primary transverse process and to the adjacent transverse process), snake 40 is removed from snake sheath 60 and bone graft material inserted therein. This process will be discussed in greater detail below.

Figure 6:
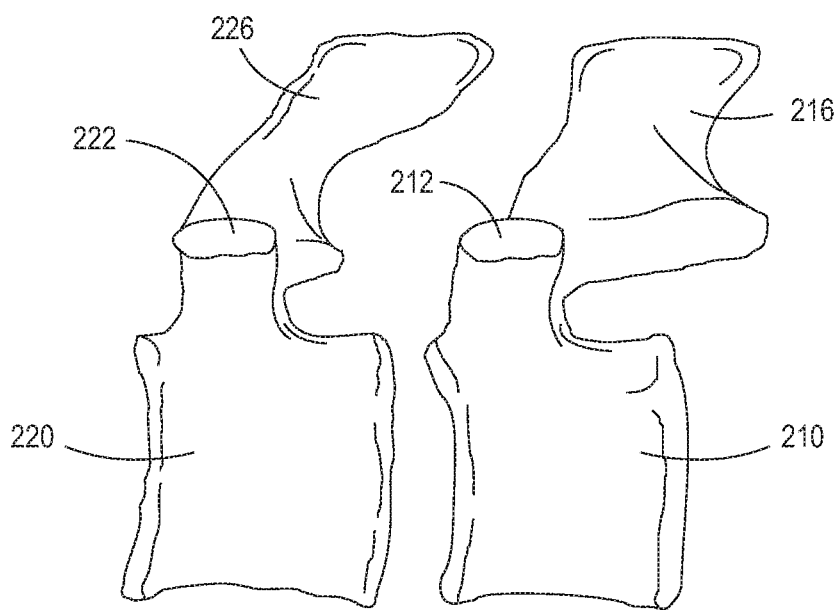
FIG. 6 is a partial side elevational view of the spinal column in FIG. 1.

FIG. 6 is a partial side elevational view of spinal column 200. In FIG. 6, vertebra 210 and vertebra 220 are shown in a longitudinal arrangement. Vertebra 220 comprises spinous process 226 and primary transverse process 222. Vertebra 210 comprises spinous process 216 and adjacent transverse process. The following figures will reference primary transverse process 222 and adjacent transverse process 212. It should be appreciated that the present disclosure can be applied to any adjacent vertebrae for delivering bone graft material therebetween for fusion. Additionally, it should be appreciated that bone graft material does not need to be delivered between transverse processes, but rather may be delivered between adjacent facet joints, articular processes, or other bone portions.

Figure 7:
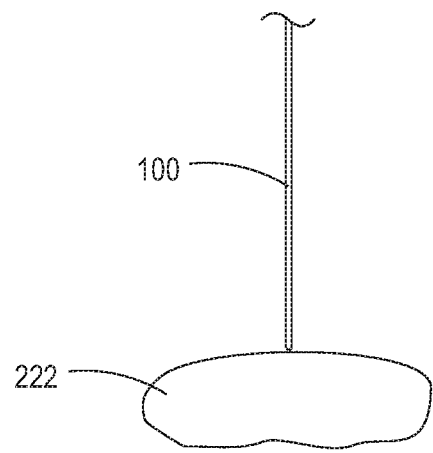
FIG. 7 is a cross-sectional view of a K-wire placed percutaneously onto a first transverse process.
Figure 8:
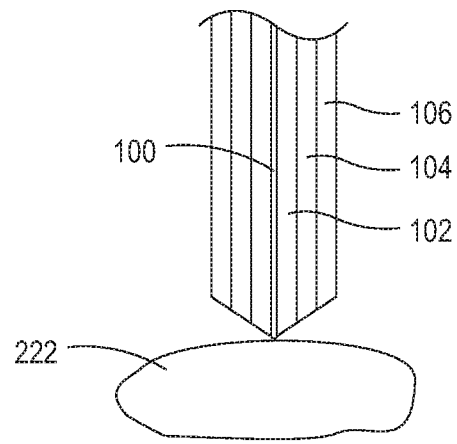
FIG. 8 is a cross-sectional view of the first transverse process shown in FIG. 7 with sequential dilators arranged over the K-wire.

FIG. 7 is a cross-sectional view of K-wire 100 placed percutaneously onto primary transverse process 222. FIG. 8 is a cross-sectional view of primary transverse process ix) 222 with sequential dilators arranged over K-wire 100. First, dilator 102 is inserted along K-wire 100 down to primary transverse process 222. Then, dilator 104 is inserted along dilator 102 down to primary transverse process 222. Then dilator 106 is inserted along dilator 104 down to primary transverse process 222. It should be appreciated that any number of dilators suitable to create a sufficient sized opening down to primary transverse process 222 may be used (e.g., one or more dilators).

Figure 9:
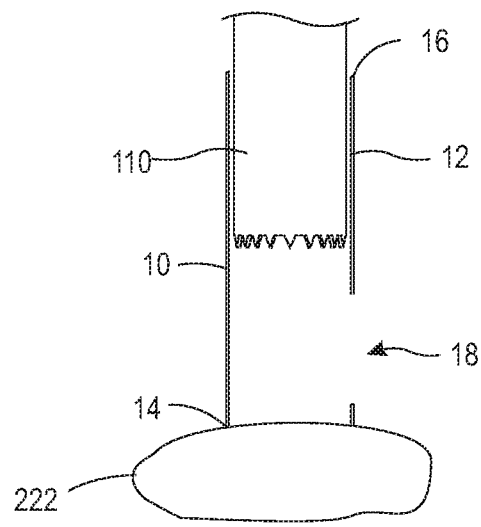
FIG. 9 is a cross-sectional view of the dilator sheath shown in FIG. 3A arranged on the first transverse process with a rasp being inserted therein.
Figure 10:
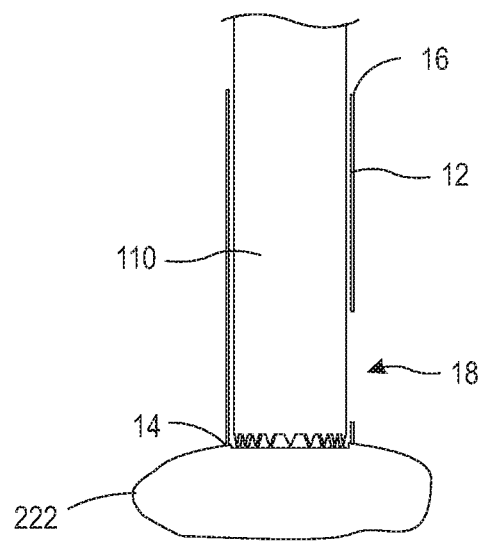
FIG. 10 is a cross-sectional view of the dilator sheath arranged on the first transverse process with the rasp engaging the first transverse process.

FIG. 9 is a cross-sectional view of dilator sheath 10 arranged on primary transverse process 222 with rasp 110 being inserted therein. Once dilator 106 is in place, dilator sheath 10 is inserted along dilator 106 down to primary transverse process 222 with window 18 directed toward adjacent transverse process 212. K-wire 100 and dilators 102, 104, and 106 are removed leaving just dilator sheath 10 in position on primary transverse process 222. End 14 of dilator sheath 10 is arranged in contact with primary transverse process 222. Subsequently, cylindrical rasp 110 is inserted in open end 16 of dilator sheath 10. FIG. 10 is a cross-sectional view of dilator sheath 10 arranged on primary transverse process with rasp 110 engaging primary transverse process 222. Rasp 110 is inserted and twisted clockwise and counter clockwise to decorticate primary transverse process 222. The process discussed above is repeated at adjacent transverse process 212.

Figure 11:
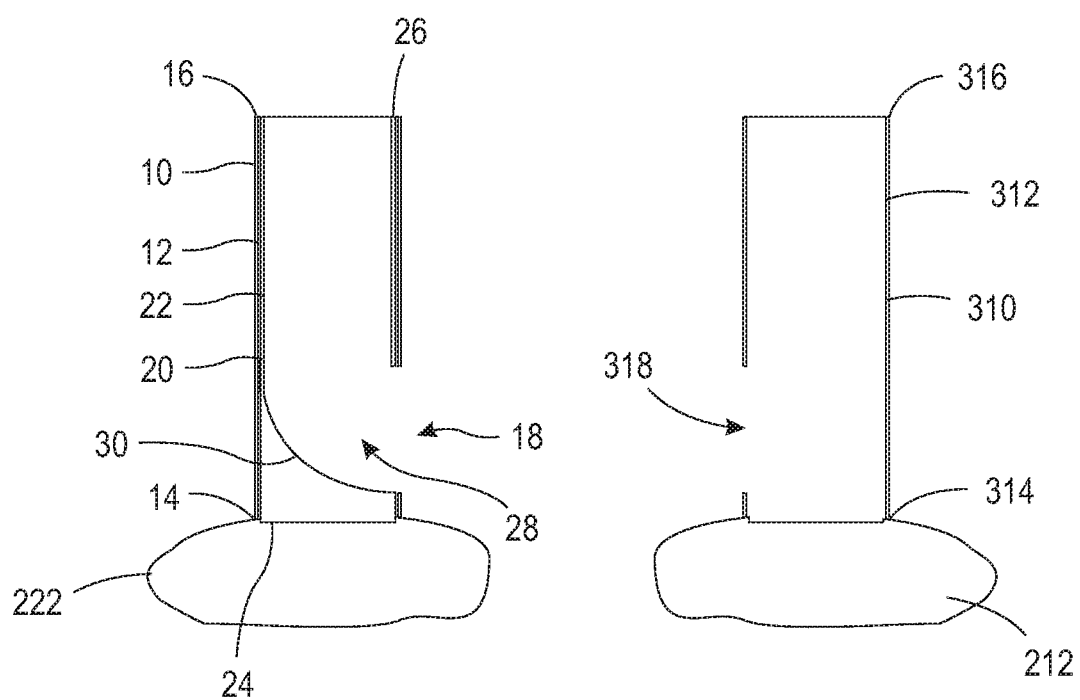
FIG. 11 is a cross-sectional view of the ramp guide shown in FIG. 2A positioned in the dilator sheath.

FIG. 11 is a cross-sectional view of ramp guide 20 positioned in dilator sheath 10. As shown, dilator sheath 10 is positioned with end 14 in contact with primary transverse process 222 and window 18 directed toward adjacent transverse process 212. Ramp guide 20 is arranged in dilator sheath 10 with end 24 in contact with primary transverse process 222 and window 28 at least partially aligned with window 18 and directed toward adjacent transverse process 212. Dilator sheath 310 is positioned with end 314 in contact with adjacent transverse process 212 and window 318 directed toward primary transverse process. Dilator sheath 310 is positioned at adjacent transverse process 212 in substantially the same way that dilator sheath 10 is positioned on primary transverse process 222, as discussed above (i.e., using a K-wire and one or more dilators). Subsequently, rasp 110 is inserted into dilator sheath 310 and used to decorticate adjacent transverse process 212.

Figure 12A:
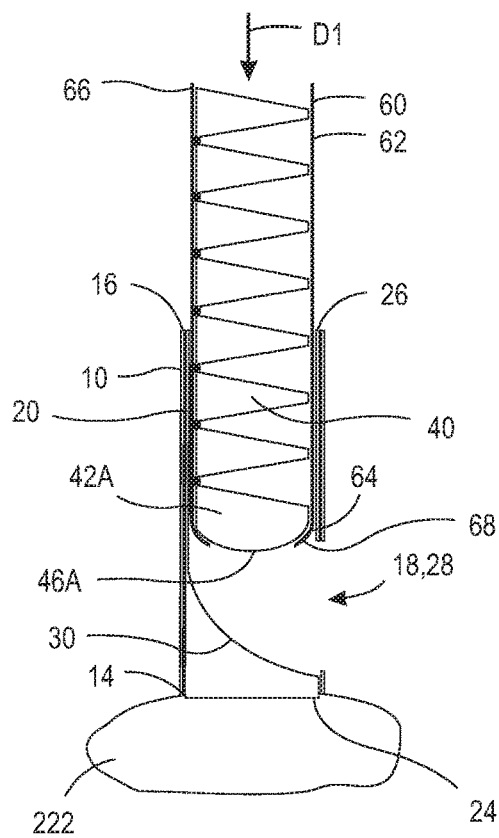
FIG. 12A is a cross-sectional view of the snake shown in FIG. 4A and snake sheath shown in FIG. 5 inserted into the ramp guide.
Figure 12B:
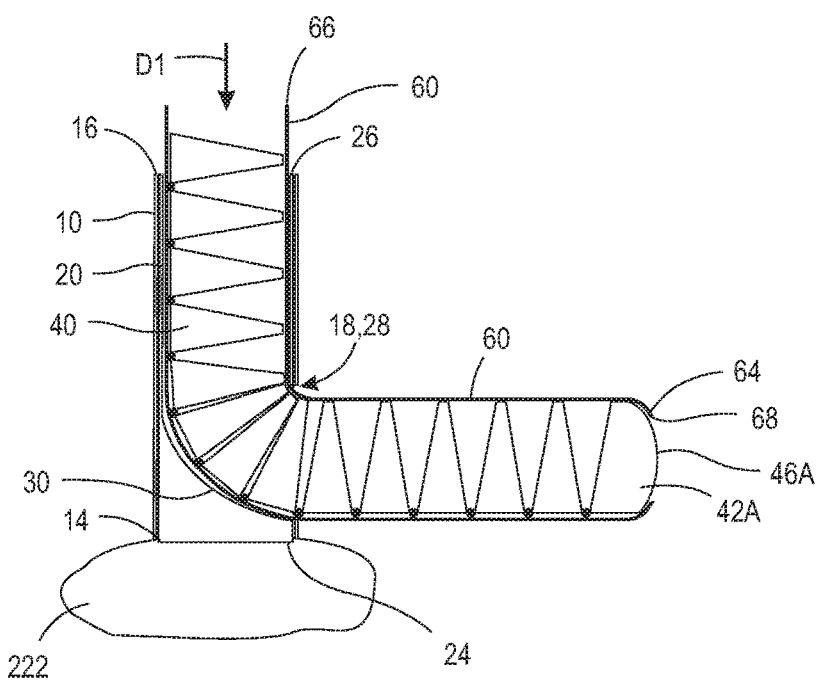
FIG. 12B is a cross-sectional view of the snake and snake sheath advanced through a window of the dilator sheath.
Figure 13:
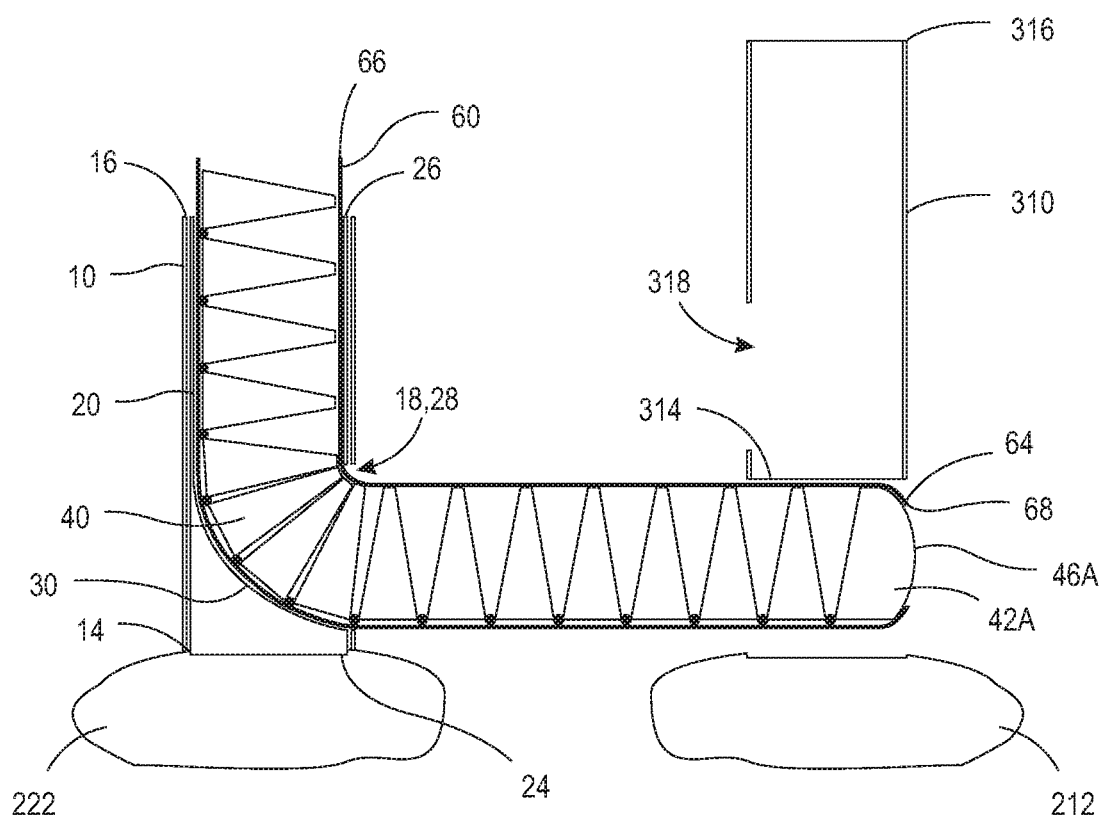
FIG. 13 is a cross-sectional view of snake and snake sheath advanced through the window of the dilator sheath to the level of an adjacent second transverse process.

FIG. 12A is a cross-sectional view of snake 40 and snake sheath 60 inserted into open end 26 of ramp guide 20 in direction D1. FIG. 12B is a cross-sectional view of snake 40 and snake sheath 60 advanced through window 18 of dilator sheath 10 (and window 28 of ramp guide 20). As shown, snake sheath 60 is arranged over snake 40 such that flange 68 of end 64 abuts against front side 46A. As snake 40 is fed down through ramp guide 20 and out of windows 18 and 28 it pulls snake sheath 60 with it. FIG. 13 is a cross-sectional view of snake 40 and snake sheath 60 advanced through windows 18 and 28 of dilator sheath 10 and ramp guide 20, respectively, to the level of adjacent transverse process 212. As shown, dilator 310 is withdrawn to allow snake 40 and snake sheath 60 to pass over adjacent transverse process 212 without impediment. End 314 of dilator sheath 310 may further act as a guide to maintain a linear path of snake 40 from primary transverse process 222 to adjacent transverse process 212. Dilator sheath 310 further acts as a line of sight such that the user can see if and when snake 40 and snake sheath 60 arrive at adjacent transverse process 212. In some embodiments, dilator sheath 310 is not withdrawn from adjacent transverse process 212 but rather snake 40 and end 64 of snake sheath 60 are fed directly into window As shown in FIGS. 12B and 13, as snake 40 is fed down ramp 30, hinges allow the sections to flex in one direction such that their respective top sides come into close proximity with each other. The restrictive hinge design of snake 40 allows it to flex or displace in one direction to make, for example, a 90° turn down ramp 30 and out windows 18 and 28.

Figure 14:
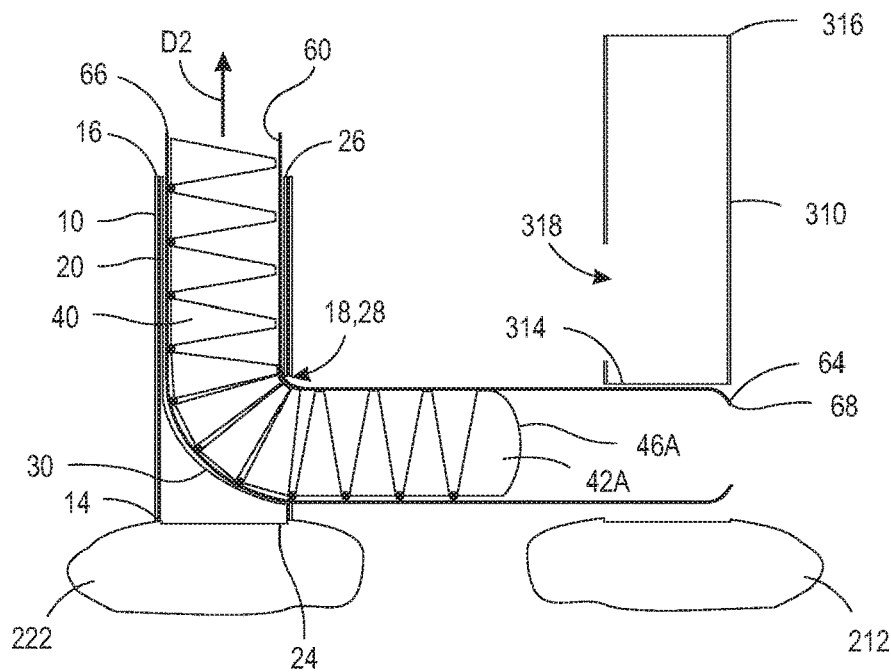
FIG. 14 is a cross-sectional view of the snake being withdrawn from the snake sheath.
Figure 15:
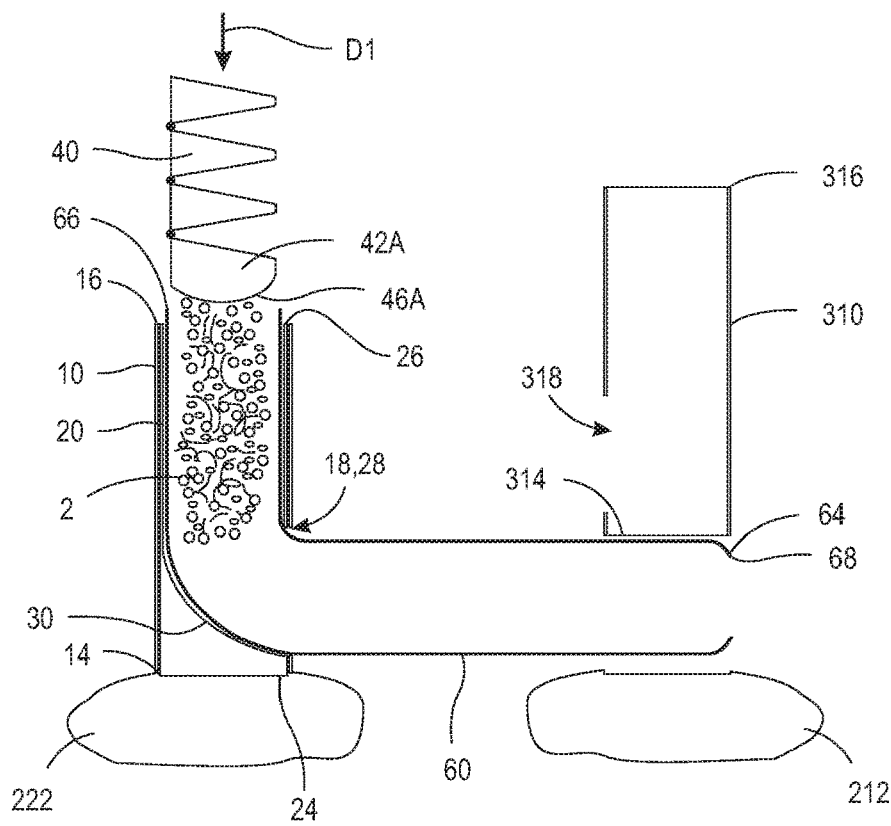
FIG. 15 is a cross-sectional view of the bone graft material being impelled along the snake sheath using the snake.
Figure 16:
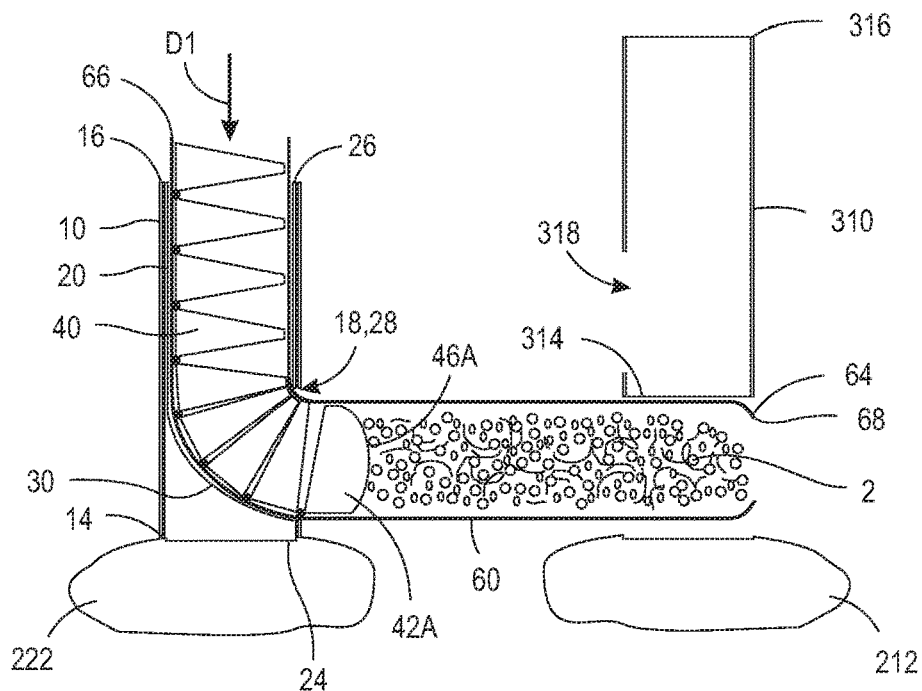
FIG. 16 is a cross-sectional view of the bone graft material arranged in the snake sheath and extending from the first transverse process to the second transverse process.

FIG. 14 is a cross-sectional view of snake 40 being withdrawn from snake sheath 60. As shown, snake sheath 60 is held in position by end 314 of dilator sheath 310 and snake 40 is withdrawn therefrom in direction D2. FIG. 15 is a cross-sectional view of bone graft material 2 being impelled along snake sheath 60 using snake 40. Once snake 40 is completely removed from snake sheath 60, which is positioned from primary transverse process 222 to adjacent transverse process 212, bone graft material 2 is inserted into open end 66 of snake sheath. Bone graft material 2 is displaced in snake sheath 60 via snake 40 in direction D1. FIG. 16 is a cross-sectional view of bone graft material 2 arranged in snake sheath 60 and extending from primary transverse process 222 to adjacent transverse process 212. Specifically, bone graft material 2 is packed in snake sheath 60 and extends from window 18 of dilator sheath 10 to adjacent transverse process 212.

Figure 17:
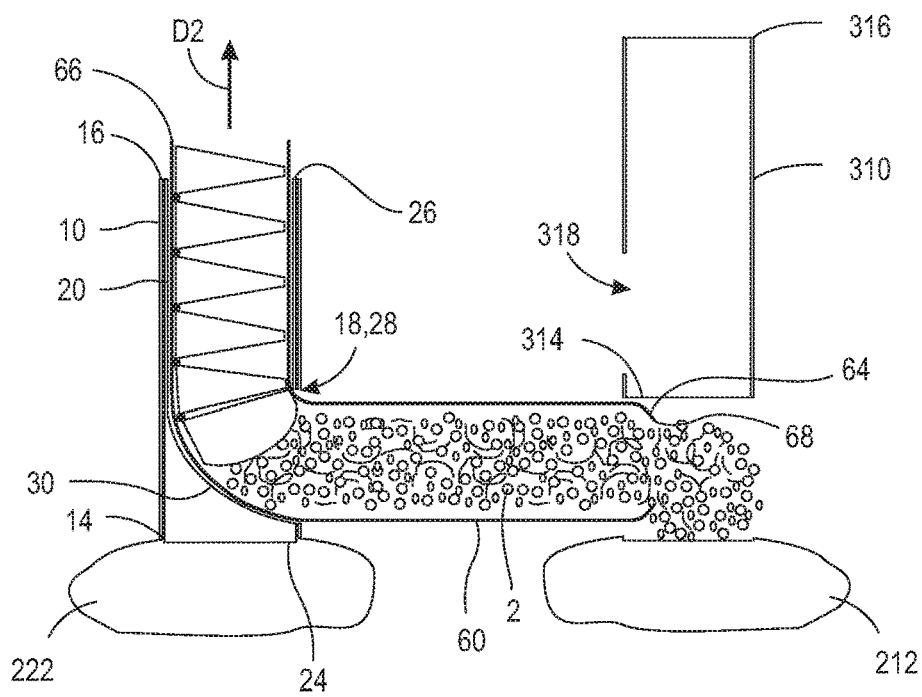
FIG. 17 is a cross-sectional view of the snake sheath being retracted about the snake leaving the bone graft material in position between the first transverse process and the second transverse process.
Figure 18:
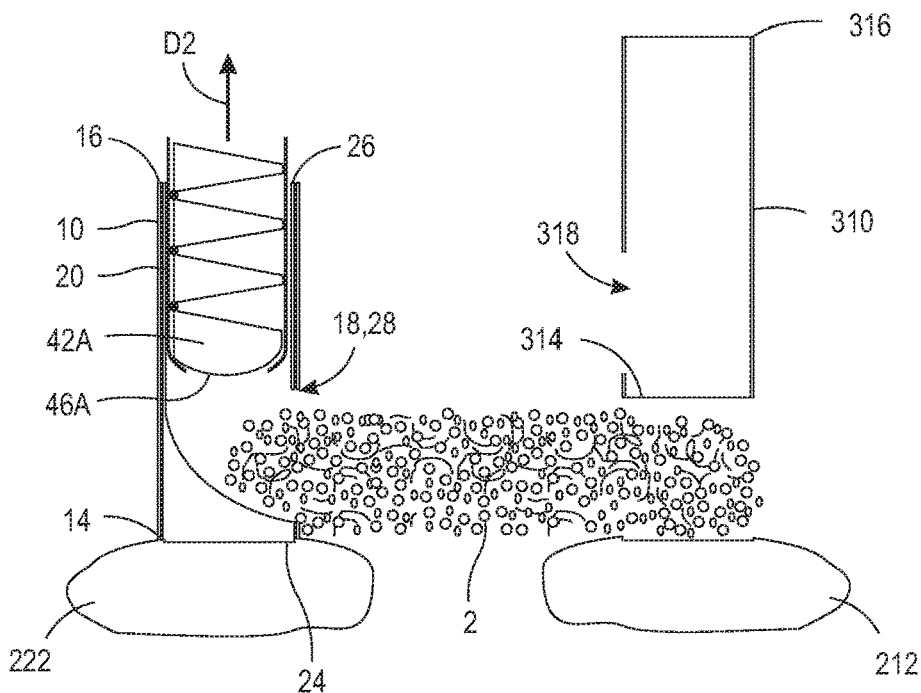
FIG. 18 is a cross-sectional view of the snake being retracted from the ramp guide.

FIG. 17 is a cross-sectional view of snake sheath 60 being retracted about snake 40 leaving bone graft material 2 in position between the primary transverse process 222 and adjacent transverse process 212. Specifically, snake 40 is held in position and end 66 of snake sheath 60 is pulled in direction D2. As such, bone graft material 2 is held in position by front end 46A of snake 40 and snake sheath 60 is removed such that it no longer encases bone graft material 2. FIG. 18 is a cross-sectional view of snake 40 being retracted from ramp guide 20 in direction D2. Once snake sheath 60 is retracted to de-case bone graft material 2, snake sheath 60 can be pulled out over snake 40 in direction D2 with snake 40 held in place. Specifically, when enough force is applied to snake sheath 60 in direction D2, flange 68 will fail allowing disengagement from front surface 46A. Alternatively, once snake sheath 60 is retracted to de-case bone graft material 2, snake 40 and snake sheath 60 can be pulled out of ramp guide 20 together in direction D2.

Figure 19:
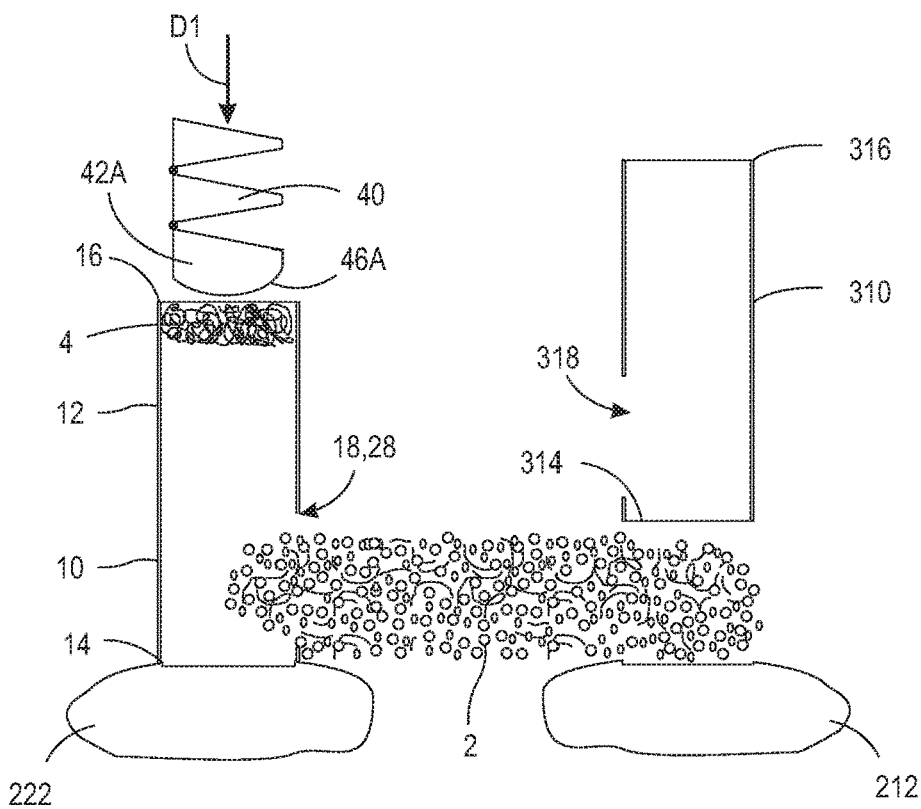
FIG. 19 is a cross-sectional view of the dilator sheath with the ramp guide removed and additional bone graft material being impacted onto the first transverse process; and, FIG. 20 is an elevational view of the bone graft material held in apposition to the first transverse process and the second transverse process by surrounding paraspinal muscle tissue.
Figure 20:
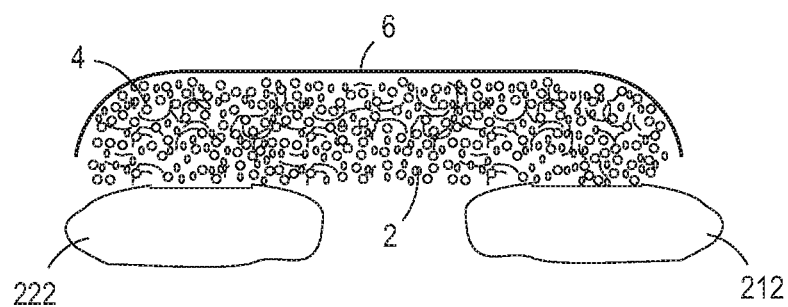

FIG. 19 is a cross-sectional view of dilator sheath 10 with ramp guide 20 removed and additional bone graft material 4 being impacted onto primary transverse process 222 through dilator sheath 10. As shown, additional bone graft material 4 is being inserted into dilator sheath 10 and forced down to primary transverse process 222 via snake 40. Once additional bone graft material 4 is arranged on primary transverse process 222, snake 40 and dilator sheath 10 are removed. FIG. 20 is an elevational view of bone graft material 2 and additional bone graft material 4 held in apposition to primary transverse process 222 and adjacent transverse process 212 by surrounding paraspinal muscle tissue 6. Bone graft materials 2 and 4 may comprise real bone (e.g., autograft or autogenous, or allograft), bone graft substitutes (demineralized bone matrix (DBM), ceramic-based substitutes and synthetic bone graft extenders, bone morphogenetic proteins (BMPs), graft composites), or other special bone (xenograft). In an example embodiment, bone graft materials 2 and 4 achieve bony growth and permanent fixation with hardenable materials such as bone putty or methyl methylacrylate (MMA), as is known to those having ordinary skill in the art.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

2 Bone graft material
4 Bone graft material
6 Paraspinal muscle tissue
10 Dilator sheath
12 Lateral wall
14 End
16 End
18 Window
20 Ramp guide
22 Lateral wall
24 End
26 End
28 Window
30 Ramp
40 Snake
42A Section
42B Section
42C Section
42D Section
42E Section
42F Section
42G Section
4211 Section
44A Bottom side
44B Bottom side
44C Bottom side
44D Bottom side
44E Bottom side
44F Bottom side
44G Bottom side
44H Bottom side
46A Front side
46B Front side
46C Front side
46D Front side
46E Front side
46F Front side
46G Front side
46H Front side
48A Rear side
48B Rear side
48C Rear side
48D Rear side
48E Rear side
48F Rear side
48G Rear side
48H Rear side
50A Top side
50B Top side
50C Top side
50D Top side
50E Top side
50F Top side 50G Top side
50H Top side
52A Hinge
52B Hinge
52C Hinge
52D Hinge
52E Hinge
52F Hinge
52G Hinge
54 Cord
56 End
58 End
60 Snake sheath
62 Lateral wall
64 End
66 End
68 Flange
100 Kirschner wire (K-wire)
102 Dilator
104 Dilator
106 Dilator
200 Spinal column
210 Vertebra
212 Transverse process
214 Transverse process
216 Spinous process
220 Vertebra
222 Transverse process
224 Transverse process
226 Spinous process
230 Vertebra
232 Transverse process
234 Transverse process
236 Spinous process
240 Vertebra
242 Transverse process
244 Transverse process
246 Spinous process
310 Dilator sheath
312 Lateral wall
314 End
316 End
318 Window
D1 Direction
D2 Direction

What is claimed is:

1. A bone graft delivery device, comprising:
a dilator sheath arranged to be connected to a first transverse process, the dilator sheath having a first window;
a ramp guide removably engageable with the dilator sheath and arranged to be connected to the first transverse process, the ramp guide comprising a second window and a ramp at least partially connected to the second window;
a snake sheath; and,
a snake arranged to feed the snake sheath through the ramp guide and out of the first and second windows toward a second transverse process, the second transverse process being adjacent to the first transverse process.

2. The bone graft delivery device as recited in claim 1, wherein when the ramp guide is engaged with the dilator sheath, the second window is at least partially aligned with the first window.

3. The bone graft delivery device as recited in claim 1, wherein the ramp guide comprises:
a lateral wall;
a first end; and,
a second end;
wherein the second window is arranged between the first and second ends.

4. The bone graft delivery device as recited in claim 3, wherein the ramp is arranged within the lateral wall.

5. The bone graft delivery device as recited in claim 1, wherein the ramp guide and/or the dilator sheath are cylindrical.

6. The bone graft delivery device as recited in claim 1, wherein the snake comprises a plurality of sections and one or more hinges connecting the plurality of sections.

7. The bone graft delivery device as recited in claim 6, wherein:
the plurality of sections comprises a first section and a second section; and,
the one or more hinges comprises a first hinge.

8. The bone graft delivery device as recited in claim 7, wherein:
the first section comprises:
a first bottom side;
a first front side;
a first rear side; and,
a first top side; and,
the second section comprises:
a second bottom side hingedly connected to the first bottom side via the first hinge;
a second front side arranged proximate the first rear side;
a second rear side; and,
a second top side.

9. The bone graft delivery device as recited in claim 8, wherein the first hinge allows displacement of the first bottom side relative to the second bottom side in a first circumferential direction and in a second circumferential direction, opposite the first circumferential direction.

10. The bone graft delivery device as recited in claim 9, wherein in a fully open position:
the first bottom side is aligned with the second bottom side; and,
the first hinge prevents displacement of the first bottom side relative to the second bottom side in the second circumferential direction.

11. The bone graft delivery device as recited in claim 8, wherein the first front side is curvilinear.

12. The bone graft delivery device as recited in claim 7, wherein the first section is arranged to engage a leading flange of the snake sheath.

13. The bone graft delivery device as recited in claim 12, wherein a first front side of the first section is arranged to engage the leading flange.

14. The bone graft delivery device as recited in claim 7, wherein the snake further comprises a cord connected to the first section.

15. The bone graft delivery device as recited in claim 1, further comprising a second dilator sheath arranged to be connected to the second transverse process, wherein the snake feeds the snake sheath from the dilator sheath to the second dilator sheath.

16. A bone graft delivery device, comprising:
a dilator sheath arranged to be connected to a first transverse process, the dilator sheath having a first window arranged to be directed to a second transverse process, the second transverse process being adjacent to the first transverse process;

a ramp guide removably engageable with the dilator sheath and arranged to be connected to the first transverse process, the ramp guide comprising:
  a lateral wall;
  a first end;
  a second end;
  a second window arranged between the first and second ends; and;
  a ramp at least partially connected to the second window and arranged within the lateral wall;
a snake sheath; and,
a snake arranged to feed the snake sheath through the ramp guide and out of the first and second windows to the second transverse process.

17. The bone graft delivery device as recited in claim 16, wherein when the ramp guide is engaged with the dilator sheath, the second window is at least partially aligned with the first window.

18. The bone graft delivery device as recited in claim 16, wherein the snake comprises at least two sections hingedly connected together, the at least two sections comprising:
  a first section, including:
    a first bottom side;
    a first front side;
    a first rear side; and,
    a first top side; and,
  a second section, including:
    a second bottom side hingedly connected to the first bottom side via a first hinge;
    a second front side arranged proximate the first rear side;
    a second rear side; and,
    a second top side.

19. The bone graft delivery device as recited in claim 18, wherein the first hinge connects the first and second sections and allows displacement of the first bottom side relative to the second bottom side in a first circumferential direction and in a second circumferential direction, opposite the first circumferential direction.

20. The bone graft delivery device as recited in claim 19, wherein in a fully open position:
  the first bottom side is aligned with the second bottom side; and,
  the first hinge prevents displacement of the first bottom side relative to the second bottom side in the second circumferential direction.

* * * * *